United States Patent [19]

Riebli et al.

[11] Patent Number: 4,992,458
[45] Date of Patent: Feb. 12, 1991

[54] 1-PHENOXYPHENYL-1-TRIAZOLYLMETHYL-CARBINOL COMPOUND AS MICROBICIDES

[75] Inventors: Peter Riebli, Buckten; Adolf Hubele, Magden, both of Switzerland

[73] Assignee: Ciba-Geigy Corporation, Ardsley, N.Y.

[21] Appl. No.: 376,185

[22] Filed: Jul. 6, 1989

Related U.S. Application Data

[63] Continuation of Ser. No. 143,985, Jan. 14, 1988, abandoned.

[30] Foreign Application Priority Data

Jan. 21, 1987 [CH] Switzerland ............................ 214/87

[51] Int. Cl.$^5$ ................. A01N 43/653; C07D 249/08
[52] U.S. Cl. ................... 514/383; 548/268.6
[58] Field of Search ............ 514/383; 548/268, 268.6

[56] References Cited

U.S. PATENT DOCUMENTS 4,582,843  4/1986  Timmler et al. .................... 548/262

FOREIGN PATENT DOCUMENTS 0000017  12/1978  European Pat. Off. .
0000018  12/1978  European Pat. Off. .
0077479  4/1983   European Pat. Off. .
0126430  11/1984  European Pat. Off. .
2628419  1/1978   Fed. Rep. of Germany .
2064520  6/1981   United Kingdom ............... 548/262

OTHER PUBLICATIONS

Lantzsch et al., "Hydroxyethylazoles as, Etc.", CA 107:59043x (1987).

*Primary Examiner*—Glennon H. Hollrah
*Assistant Examiner*—Patricia L. Morris
*Attorney, Agent, or Firm*—George R. Dohmann

[57] ABSTRACT

Novel 1-phenoxyphenyl-1-triazolylmethyl-carbinols of formula I

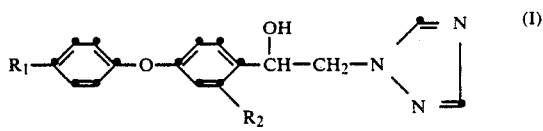

in which $R_1$ is fluorine, chlorine or bromine and $R_2$ is fluorine, chlorine, bromine or methyl, and the phytophysiologically tolerable acid addition salts thereof have excellent microbicidal, in particular phytofungicidal, properties. They can be used for controlling and/or preventing infections caused by microorganisms in useful plants. The preparation of these compounds and compositions containing them is described.

8 Claims, No Drawings

1-PHENOXYPHENYL-1-TRIAZOLYLMETHYL-CARBINOL COMPOUND AS MICROBICIDES

This application is a continuation, of application Ser. No. 143,985, filed 1/14/88, abandoned.

The present invention relates to novel 1-phenoxyphenyl-1-triazolylmethyl-carbinols of formula I and to a microbicidal composition which contains, as active ingredient, at least one compound of formula I below or an acid addition compound thereof, to the preparation of those compounds or the compositions containing them, and to methods of controlling or preventing attacks on plants by phytopathogenic microorganisms.

The 1-phenoxyphenyl-1-triazolylmethylcarbinols have the formula I

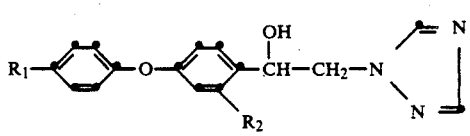

wherein
$R_1$ is fluorine, chlorine or bromine and
$R_2$ is fluorine, chlorine, bromine or methyl,
and acid addition salts of these compounds with phytophysiologically tolerable organic and inorganic acids.

Suitable acids for forming acid addition salts with compounds of formula I are any organic and inorganic acids provided they form phytophysiologically tolerable salts.

Examples of acid addition salt-forming acids are inorganic acids: hydrohalic acid such as hydrofluoric acid, hydrochloric acid, hydrobromic acid or hydriodic acid, and also sulphuric acid, phosphoric acid, phosphorous acid and nitric acid, and organic acids such as acetic acid, trifluoroacetic acid, trichloroacetic acid, propionic acid, tartaric acid, glycolic acid, lactic acid, succinic acid, citric acid, benzoic acid, cinnamic acid, oxalic acid, formic acid, benzenesulphonic acid, p-toluenesulphonic acid, methanesulphonic acid, salicylic acid, p-aminosalicylic acid, 2-phenoxybenzoic acid or 2-acetoxybenzoic acid. These acids are added to the relevant free compounds of formula I in accordance with methods known per se.

The compounds of formula I are stable at room temperature. They can be used in the agricultural sector or related fields, in particular preventively and curatively, for controlling phytopathogenic microorganisms. The compounds of formula I are distinguished by very good fungicidal action and easy application in a wide range of concentrations.

The compounds of formula I have pronounced microbicidal activity. The formula covers the following 12 compounds:

2-[4-(4-fluorophenoxy)-2-fluorophenyl]-1-(1H-1,2,4-triazol-1-yl)-ethan-2-ol,
2-[4-(4-fluorophenoxy)-2-chlorophenyl]-1-(1H-1,2,4-triazol-1-yl)-ethan-2-ol,
2-[4-(4-fluorophenoxy)-2-bromophenyl]-1-(1H-1,2,4-triazol-1-yl)-ethan-2-ol,
2-[4-(4-fluorophenoxy)-2-methylphenyl]-1-(1H-1,2,4-triazol-1-yl)-ethan-2-ol,
2-[4-(4-chlorophenoxy)-2-fluorophenyl]-1-(1H-1,2,4-triazol-1-yl)-ethan-2-ol,
2-[4-(4-chlorophenoxy)-2-chlorophenyl]-1-(1H-1,2,4-triazol-1-yl)-ethan-2-ol,
2-[4-(4-chlorophenoxy)-2-bromophenyl]-1-(1H-1,2,4-triazol-1-yl)-ethan-2-ol,
2-[4-(4-chlorophenoxy)-2-methylphenyl]-1-(1H-1,2,4-triazol-1-yl)-ethan-2-ol,
2-[4-(4-bromophenoxy)-2-fluorophenyl]-1-(1H-1,2,4-triazol-1-yl)-ethan-2-ol,
2-[4-(4-bromophenoxy)-2-chlorophenyl]-1-(1H-1,2,4-triazol-1-yl)-ethan-2-ol,
2-[4-(4-bromophenoxy)-2-bromophenyl]-1-(1H-1,2,4-triazol-1-yl)-ethan-2-ol,
2-[4-(4-bromophenoxy)-2-methylphenyl]-1-(1H-1,2,4-triazol-1-yl)-ethan-2-ol
and salts thereof with phytophysiologically tolerable organic and inorganic acids.

The 12 phenoxyphenyl-1-triazole-carbinols of formula I are novel. Compounds having a similar constitution and microbicidal-fungicidal action have been disclosed in EP-A No. 77 479. However, that document mentions only diphenyl ether derivatives in which the central phenyl ring contains no other substituents. The compounds according to the invention, in which the central phenyl ring is substituted by $R_2$, are distinguished by remarkably improved phytofungicidal action and can therefore be used in extremely low rates of application. The above reference would not give the person skilled in the art any indication that the compounds of formula I according to the invention are extraordinarily effective fungicides.

The phenoxytriazolecarbinols of formula I are prepared by condensing a phenoxyacetophenone of formula II with 1H-1,2,4-triazole of formula III or with a metal salt thereof in accordance with the equation

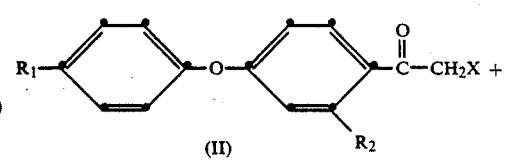

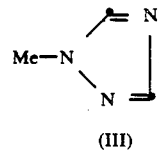

In these formulae, $R_1$ and $R_2$ have the meanings given under formula I, Me is hydrogen or a metal cation and X is a nucleofugic leaving group, e.g. halogen, especially chlorine, bromine or iodine, but also a benzenesulphonyloxy, p-tosyloxy, trifluoroacetoxy or preferably a lower alkylsulphonyloxy, such as mesyloxy, group. The resulting 2-(diphenyl ether)-1-(1H-1,2,4-triazol)-ethan-2-ones of formula IV

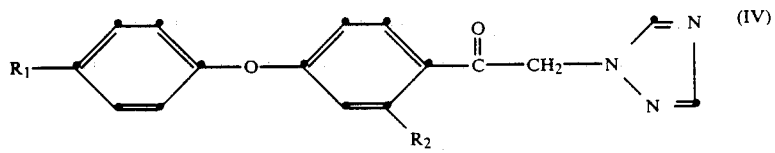

in which $R_1$ and $R_2$ have the meanings given under formula I are then reduced with hydrogen or a hydrogen donor to form compounds of formula I.

If an acetophenone halide of formula II and 1H-1,2,4-triazole are used for the reaction, the reaction is advantageously carried out in the presence of a base and a catalytic amount of potassium iodide in a ketone as solvent.

The solvent should be non-aqueous and may be acetone, methyl ethyl ketone or cyclohexanone. Apart from ketones, suitable solvents are also ethers such as diethyl ether, dioxane or tetrahydrofuran.

There is used as base a tertiary amine such as triethylamine or methylpyridine, or alternatively an inorganic base, preferably an alkali metal carbonate or hydrogen carbonate.

The reduction is carried out in an inert organic solvent in the presence of hydrogen or preferably a hydrogen donor such as sodium borohydride or lithium aluminium hydride.

In the course of the reduction or hydrogenation reactions of the ketone compounds of formula IV to form carbinols of formula I, R,S-mixtures of stereoisomers are formed whose composition depends on the catalyst used for the hydrogenation or on the reducing agent.

The solvents used here are the above-mentioned ethers or alternatively lower alkanols such as methanol, ethanol, propanol and isopropanol.

The temperatures in these reactions are from 0° C. up to the boiling point of the reaction mixture.

The starting materials of formula II are known or can be obtained in a manner known per se by condensing a 4-haloacetophenone with a phenol or by condensing a 4-hydroxyacetophenone with a halobenzene, and then halogenating, in accordance with the equation manner, e.g. by the fractional crystallisation of salts of optically active strong acids. The two enantiomers may have different biological activities.

The present invention relates to all the pure enantiomers and mixtures thereof with one another.

Surprisingly, it has been found that the compounds of formula I have, for practical field application purposes, a very advantageous microbicidal spectrum against phytopathogenic fungi and bacteria. Compounds of formula I have very advantageous curative, systemic and, in particular, preventive properties, and can be used for protecting numerous cultivated plants. With the compounds of formula I it is possible to inhibit or destroy the microorganisms which occur in plants or in parts of plants (fruit, blossoms, leaves, stems, tubers, roots) in different crops of useful plants, while at the same time the parts of plants which grow later are also protected from attach by such microorganisms.

The compounds of formula I are effective against the phytopathogenic fungi belonging to the following classes: Fungi imperfecti (e.g. Botrytis, Helminthosporium, Fusarium, Septoria, Cercospora, Alternaria); Basidiomycetes (e.g. the genera Hemileia, Rhizoctonia, Puccinia); and, in particular, against the class of the Ascomycetes (e.g. Venturia, Podosphaera, Erysiphe, Monilinia, Uncinula). In addition, the compounds of formula I have a systemic action. They can also be used as dressing agents for protecting seeds (fruit, tubers, grains) and plant cuttings against fungus infections as well as against phytopathogenic fungi which occur in the soil.

The compounds of this invention are particularly well tolerated by plants.

The invention also relates to the use of the compounds of formula I for controlling phytopathogenic

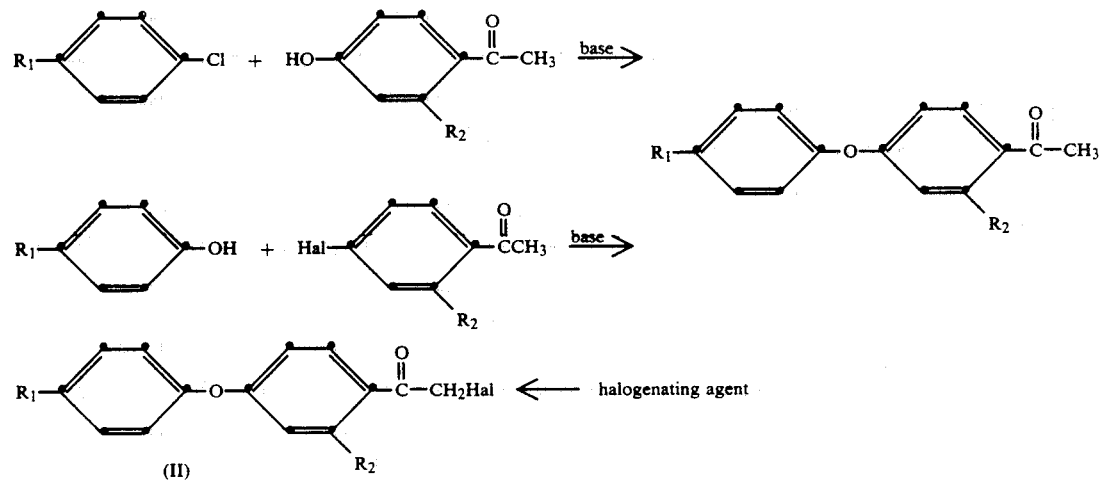

The carbinols of formula I have a chiral centre and may occur in R- and S-form.

A mixture of the two enantiomers is normally formed when these compounds are prepared. This mixture can be resolved into the pure optical antipodes in customary microorganisms, in particular phytopathogenic fungi, or for protecting plants from attack by said microorganisms.

The present invention further embraces the preparation of agro-chemical compositions, which comprises homogeneously mixing the active ingredient with one or more compounds or groups of compounds described herein. The invention furthermore relates to a method of treating plants, which comprises applying thereto the compounds of formula I or the novel compositions.

Target crops to be protected within the scope of the present invention comprise e.g. the following species of plants: cereals (wheat, barley, rye, oats, rice, sorghum and related crops), beet (sugar beet and fodder beet), pomes, drupes and soft fruit (apples, pears, plums, peaches, almonds, cherries, strawberries, raspberries, cranberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, pineapple, tea, vines, hops, bananas and natural rubber plants, as well as ornamentals (flowers, shrubs, deciduous trees and conifers). This recitation constitutes no limitation.

The compounds of formula I are normally applied in the form of compositions and can be applied to the crop area or plant to be treated, simultaneously or in succession, with further compounds. These compounds can be both fertilisers or micronutrient donors or other preparations that influence plant growth. They can also be selective herbicides, insecticides, fungicides, bactericides, nematicides, molluscicides or mixtures of several of these preparations, if desired together with further carriers, surfactants or application promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I, or an agro-chemical composition which contains at least one of said compounds, is foliar application. The number of applications and the rate of application depend on the risk of infestation by the corresponding pathogen (species of fungus). However, the compounds of formula I can also penetrate the plant through the roots via the soil (systemic action) by impregnating the locus of the plant with a liquid formulation, or by applying the compounds in solid form to the soil, e.g. in granular form (soil application). The compounds of formula I may also be applied to seeds (coating) by impregnating the seeds either with a liquid formulation containing a compound of formula I, or coating them with a solid formulation. In special cases, further types of application are also possible, e.g. selective treatment of the plant stems or buds.

The compounds of formula I are used in unmodified form or, preferably, together with the adjuvants conventionally employed in the art of formulation, and are therefore formulated in known manner e.g. to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 100 g to 600 g a.i./ha.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulphoxide or dimethylformamide, as well as vegetable oils or epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both so-called water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Mention may also be made of fatty acid methyllaurin salts.

More frequently, however, so-called synthetic surfactants are used, especially fatty alcohol sulphonates, fatty alcohol sulphates, sulphonated benzimidazole derivatives or alkylsulphonates.

The fatty alcohol sulphonates or sulphates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulphonic acid, of dodecylsulphate or of a mixture of fatty alcohol sulfates obtained from natural fatty acids. These compounds also comprise the salts of sulphated and sulphonated fatty alcohol/ethylene oxide adducts. The sulphonated benzimidazole derivatives preferably contain 2 sulphonic acid groups and one fatty acid radical containing 8 to 22 carbon atoms. Examples of alkylarylsulphonates are the sodium, calcium or triethanolamine salts of dodecylbenzenesulphonic acid, dibutylnaphthalenesulphonic acid, or of a condensate of naphthalenesulphonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenol-polyethoxyethanols, castor oil polyglycol ethers, polypropylene/polyethylene oxide adducts, tributylphenoxypolyethyleneethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methylsulphates or ethylsulphates, e.g. stearyltrimethylammonium chloride or benzyldi(2-chloroethyl)ethyl-ammonium bromide.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

Such agrochemical compositions constitute an object of the present invention.

The following Example describes the preparation of a compound of formula I. In this Example, temperatures are indicated in degrees Celsius and pressures are indicated in millibars (mbar).

1. PREPARATION EXAMPLES 1.1 Preparation of 2-[4-(4-bromophenoxy)-2-chlorophenyl]-1-(1H-1,2,4-triazol-1-yl)-ethan-2-ol

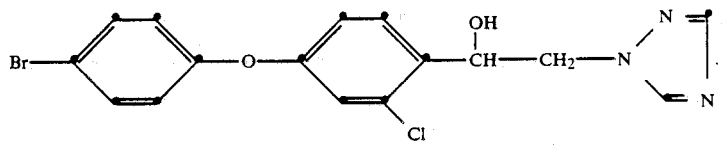

While stirring and passing a current of nitrogen through the reaction mixture, 0.56 g (14.7 mmol) of sodium borohydride is added in portions at room temperature and within a period of 15 minutes to a solution of 5.8 g (14.7 mmol) of 2-[4-(4-bromophenoxy)-2-chlorophenyl]-1-(1H-1,2,4-triazol-1-yl)-ethan-2-one in 40 ml of methanol. The temperature of the reaction mixture rises from 22° to 38°. When the addition is complete, stirring is continued for a further 4 hours at room temperature and then 2.2 g of concentrated hydrochloric acid are added, followed somewhat later by the addition of 22 ml of 10% sodium hydrogen carbonate solution. The title compound is precipitated in crystalline form. It is isolated by filtration, washed with water and dried, to give 5.5 g of 2-[4-(4-bromophenoxy)-2-chlorophenyl]-1-(1H-1,2,4-triazol-1-yl)-ethan-2-ol om the form of a beige crystalline powder. Melting point 115°-118° C.

The 2-[4-(4-bromophenoxy)-2-chlorophenyl]-1-(1H-1,2,4-triazol-1-yl)-ethan-2-one required as starting material is prepared in the following manner:

A mixture of 8.7 g (21.5 mmol) of 2-[4-(4-bromophenoxy)-2-chlorophenyl]-1-2-one, 1.63 g (23.7 mmol) of 1,2,4-triazole, 3.26 g (23.7 mmol) of potassium carbonate and a catalytically effective amount of 0.3 g of potassium iodide in 80 ml of absolute butan-2-one is stirred for 24 hours at room temperature. A further 0.15 g (2.1 mmol) of 1,2,4-triazole is then added and the batch is heated for 6 hours at 45° with stirring. After cooling to room temperature, the reaction mixture is filtered, the filtrate is treated with activated carbon, filtered again and concentrated in a rotary evaporator. The residue is recrystallised from ethanol, to give 2-[4-(4-bromophenoxy)-2-chlorophenyl]-1-(1H-1,2,4-triazol)-ethan-2-one as a beige-white crystalline powder which melts at 171°-173°.

The compounds listed in Table 1 are prepared in the same manner.

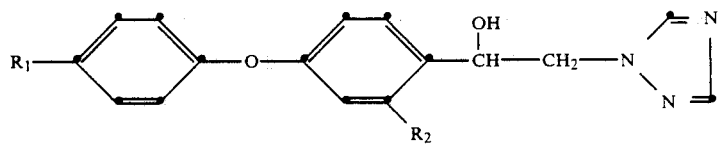

TABLE 1

| No. | $R_1$ | $R_2$ | physical data |
| --- | --- | --- | --- |
| 1. | F | F | m.p. 117–119 |
| 2. | F | Cl | m.p. 110–111 |
| 3. | F | Br | m.p. 115–117 |
| 4. | F | $CH_3$ | m.p. 102–103 |
| 5. | Cl | F | |
| 6. | Cl | Cl | m.p. 94–96 |
| 7. | Cl | Br | m.p. 108–110 |
| 8. | Cl | $CH_3$ | m.p. 107–108 |
| 9. | Br | F | |
| 10. | Br | Cl | m.p. 115–118 |
| 11. | Br | Br | m.p. 115–117 |
| 12. | Br | $CH_3$ | m.p. 119–121 |

2. FORMULATION EXAMPLES FOR SOLID ACTIVE INGREDIENTS OF FORMULA I
(throughout, percentages are by weight)

2.1. Wettable powders

| | (a) | (b) | (c) |
| --- | --- | --- | --- |
| a compound of Table 1 | 25% | 50% | 75% |
| sodium lignosulphonate | 5% | 5% | — |
| sodium lauryl sulphate | 3% | — | 5% |
| sodium diisobutylnaphthalene-sulphonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

2.2. Emulsifiable concentrate

| | |
| --- | --- |
| a compound of Table 1 | 10% |
| octylphenol polyethylene glycol ether (4–5 moles of ethylene oxide) | 3% |
| calcium dodecylbenzenesulphonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

2.3. Dusts

| | (a) | (b) |
| --- | --- | --- |
| a compound of Table 1 | 5% | 8% |
| talcum | 95% | — |
| kaolin | — | 92% |

Ready-for-use dusts are obtained by mixing the active ingredient with the carrier, and grinding the mixture in a suitable mill.

2.4. Extruder granulate

| | |
| --- | --- |
| a compound of Table 1 | 10% |
| sodium lignosulphonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

2.5. Coated granulate

| | |
| --- | --- |
| a compound of Table 1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

2.6. Suspension concentrate

| | |
| --- | --- |
| a compound of Table 1 | 40% |
| ethylene glycol | 10% |
| nonylphenol polyethylene glycol ether (15 moles of ethylene oxide) | 6% |
| sodium lignosulphonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. BIOLOGICAL EXAMPLES

Example 3.1

Action against *Puccinia graminis* on wheat (a) Residual protective action

Wheat plants are treated 6 days after sowing with a spray mixture (0.006% active ingredient) prepared from a wettable powder formulation of the test compound. After 24 hours the treated plants are infected with a uredospore suspension of the fungus. The infected plants are incubated for 48 hours at 95–100% relative humidity and about 20° C. and then stood in a greenhouse at about 22° C. Evaluation of rust pustule development is made 12 days after infection.

(b) Systemic action

Wheat plants are treated 5 days after sowing with a spray mixture (0.002% active ingredient, based on the volume of the soil) prepared from a wettable powder formulation of the test compound. After 48 hours the treated plants are infected with a uredospore suspension of the fungus. The infected plants are then incubated for 48 hours at 95–100% relative humidity and about 20° C. and then stood in a greenhouse at about 22° C. Evaluation of rust pustule development is made 12 days after infection.

Compounds of Table 1 inhibit Puccinia attack almost completely (0 to 10% attack). On the other hand, Puccinia attack is 100% on untreated and infected control plants.

Example 3.2

Action against *Cercospora arachidicola* on groundnut plants

Residual protective action

Groundnut plants 10–15 cm in height are sprayed with a spray mixture (0.02% active ingredient) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and is based on the number and size of the specks.

Compared with untreated and infected control plants (number and size of the specks=100%), Cercospora attack on groundnut plants treated with compounds of the Table is substantially reduced. Thus compounds of Table 1 inhibit the occurrence of specks almost completely (0 to 10% attack).

Example 3.3

Action against *Erysiphe graminis* on barley (a) Residual protective action

Barley plants about 8 cm in height are sprayed with a spray mixture (0.02% active ingredient) prepared from a wettable powder formulation of the tet compound. The treated plants are dusted with conidia of the fungus after 3 to 4 hours. The infected barley plants are stood in a greenhouse at about 22° C. The fungus attack is evaluated after 10 days.

(b) Systemic action

A spray mixture (0.006% active ingredient, based on the volume of the soil) prepared from a wettable powder formulation of the test compound is poured onto barley plants about 8 cm in height. Care is taken that the spray mixture does not come into contact with the parts of the plants above the soil. The treated plants are dusted 48 hours later with conidia of the fungus. The infected barley plants are then stood in a greenhouse at about 22° C. and evaluation of infestation is made after 10 days.

Compounds of Table 1 exhibit good activity against Erysiphe fungi. On the other hand, Erysiphe attack is 100% on untreated and infected control plants.

Example 3.4

Residual protective action against *Venturia inaequalis* on apple shoots

Apple cuttings with 10–20 cm long fresh shoots are sprayed with a spray mixture (0.06% a.i.) prepared from a wettable powder formulation of the test compound. The plants are infected 24 hours later with a conidia suspension of the fungus. The plants are then incubated for 5 days at 90–100% relative humidity and stood in a greenhouse for a further 10 days at 20°–24° C. Scab infestation is evaluated 15 days after infection. Compounds of Table 1 exhibit good activity against Venturia. On the other hand, Venturia attack is 100% in untreated and infected shoots.

Example 3.5

Action against *Botrytis cinerea* on beans

Residual protective action

Bean plants about 10 cm in height are sprayed with a spray mixture (0.02% active ingredient) prepared from a wettable powder formulation of the test compound. After 48 hours the treated plants are infected with a conidia suspension of the fungus. The infected plants are incubated for 3 days at 95–100% relative humidity and 21° C. and then evaluated for fungus attack. Compounds of Table 1 inhibit fungus infection very strongly. On the other hand, Botrytis attack is 100% in untreated and infected control plants.

Example 3.6

Action against *Tilletia caries* in wheat

Seeds of winter wheat of the Probus variety which are artificially infected with smut spores of *Tilletia caries* (3 g of dry spore material per 1 kg of seeds) are dressed on a mixer roll with the test fungicide at a concentration of 60 ppm of active ingredient (based on the weight of the seeds). The infected and treated wheat is sown in October in the open with a seeder in plots 2 meters long and in 3 rows. Three replicates are carried out with each test compound. To determine the effectiveness of the test compounds, the percentage of ears attacked by Tilletia is assessed at the time of ear ripening.

Compounds of Table 1 exhibit good activity against Tilletia in this test and inhibited fungus attack almost completely (0 to 5% attack). On the other hand, Tilletia attack on untreated and infected control plants is 100%.

Example 3.7

Action against *Helminthosporium gramineum* on barley

Seeds of winter barley of the "Cl" variety which are naturally infected with Helminthosporium gramineum are dressed on a mixer roll with the test fungicide at a concentration of 60 ppm of active ingredient (based on the weight of the seeds). The infected and treated barley is sown in October in the open with a seeder in plots 2 meters long and in 3 rows. Three replicates are carried out with each test compound. Until evaluation is made, the test plants are cultivated under normal field conditions. To determine the effectiveness of the test compounds, the percentage of stalks attacked by Helminthosporium is assessed at the time of ear emergence.

Compounds of Table 1 exhibit good activity against Helminthosporium in this test. They inhibit fungus attack almost completely (0 to 5% attack) while Helminthosporium attack on untreated and infected control plants was 100%.

Example 3.8

The following structurally similar compounds of the prior art were tested in comparison with compounds of the present invention in accordance with the tests carried out in the biological Examples described above.

Compounds of the prior art of formula

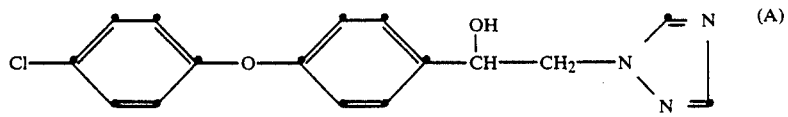

known from EP-A No. 77 479 No. 67

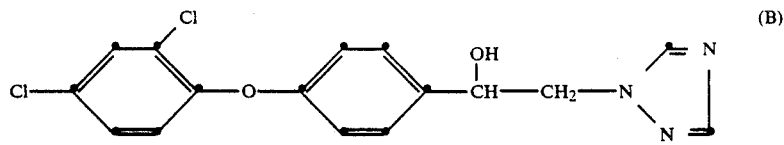

known from EP-A No. 77 479 No. 66.

BIOLOGICAL TESTS (RESIDUAL ACTION)

1. Evaluation scale

| rating | % activity | fungus attack |
|--------|------------|---------------|
| 1 | ≧95 | 0–5% |
| 3 | 80–95 | 5–20% |
| 6 | 50–80 | 20–50% |
| 9 | ≦50 | ≧50% |

A compound is considered ineffective if the fungus attack on the plant is 50% or more.

2. Test results

| Comp. | Puccinia 200/20 ppm | | Cercospora 200/20 ppm | | Erysiphe 200/20 ppm | | Venturia 200/60 ppm | |
|-------|---|---|---|---|---|---|---|---|
| A  | 9 | 9 | 9 | 9 | 3 | 6 | 9 | 9 |
| B  | 5 | 9 | 9 | 9 | 1 | 5 | 9 | 9 |
| 1  | 2 | 2 | 1 | 9 | 1 | 1 | 5 | 9 |
| 2  | 3 | 6 | 1 | 3 | 1 | 3 | 9 | 9 |
| 4  | 3 | 3 | 5 | 5 | 3 | 5 | 1 | 5 |
| 6  | 1 | 1 | 1 | 2 | 1 | 1 | 1 | 1 |
| 7  | 2 | 3 | 1 | 1 | 1 | 2 | 1 | 1 |
| 8  | 3 | 3 | 1 | 5 | 3 | 5 | 3 | 3 |
| 10 | 2 | 2 | 1 | 3 | 1 | 1 | 1 | 1 |

We claim:

1. A 1-phenoxyphenyl-1-triazolylmethyl-carbinol of formula I

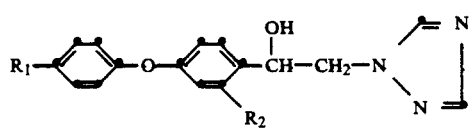

in which
R$_1$ is fluorine, chlorine or bromine,
R$_2$ is fluorine, chlorine, bromine or methyl,
and the acid addition salts with phytophysiologically tolerable organic and inorganic acids.

2. A compound according to claim 1 selected from the group consisting of
2-[4-(4-fluorophenoxy)-2-fluorophenyl]-1-(1H-1,2,4-triazol-1-yl)-ethan-2-ol;
2-[4-(4-fluorophenoxy)-2-chlorophenyl]-1-(1H-1,2,4-triazol-1-yl)-ethan-2-ol;
2-[4-(4-fluorophenoxy)-2-methylphenyl]-1-(1H-1,2,4-triazol-1-yl)-ethan-2-ol;
2-[4-(4-chlorophenoxy)-2-chlorophenyl]-1-(1H-1,2,4-triazol-1-yl)-ethan-2-ol;
2-[4-(4-chlorophenoxy)-2-bromophenyl]-1-(1H-1,2,4-triazol-1-yl)-ethan-2-ol;
2-[4-(4-chlorophenoxy)-2-methylphenyl]-1-(1H-1,2,4-triazol-1-yl)-ethan-2-ol;
2-[4-(4-bromophenoxy)-2-chlorophenyl]-1-(1H-1,2,4-triazol-1-yl)-ethan-2-ol;
2-[4-(4-bromophenoxy)-2-bromophenyl]-1-(1H-1,2,4-triazol-1-yl)-ethan-2-ol.

3. A composition for controlling or preventing attacks by microorganisms, characterized in that it contains, as active component, an effective amount of a 1-phenoxyphenyl-1-triazolylmethyl-carbinol of formula I

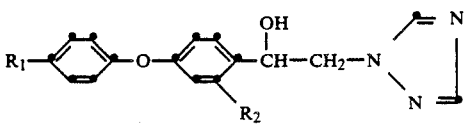

in which
R$_1$ is fluorine, chlorine or bromine and
R$_2$ is fluorine, chlorine, bromine or methyl, or
a phytophysiologically tolerable acid addition salt of such a compound, together with inert formulation adjuvants.

4. A composition according to claim 3, characterized in that it contains, as active component, at least one compound of formula I according to claim 2.

5. A composition according to claim 3, characterized in that it contains 0.1 to 99% of a compound of formula I, 99.9 to 1% of a solid or liquid adjuvant and 0 to 25% of a surfactant.

6. A composition according to claim 5, characterized in that it contains 0.1 to 95% of a compound of formula I, 99.8 to 5% of a solid or liquid adjuvant and 0.1 to 25% of a surfactant.

7. A method of controlling or preventing attacks on cultivated plants by phytopathogenic microorganisms, characterized in that an effective amount of a compound of formula I defined according to claim 1 is applied to the plant or its locus.

8. A method according to claim 7, characterized in that the microorganisms are phytopathogenic fungi.

* * * * *